(12) United States Patent  
Gibbs

(10) Patent No.: US 7,590,196 B2  
(45) Date of Patent: Sep. 15, 2009

(54) CHIRAL MIXTURE DETECTION SYSTEM USING DOUBLE REFERENCE LOCK-IN DETECTOR

(75) Inventor: Phillip R. Gibbs, Atlanta, GA (US)

(73) Assignee: Spectra Analysis, Inc.

( * ) Notice: Subject to any disclaimer, the term of this patent is extended or adjusted under 35 U.S.C. 154(b) by 732 days.

(21) Appl. No.: 11/120,723

(22) Filed: May 3, 2005

(65) Prior Publication Data

US 2005/0250465 A1   Nov. 10, 2005

(51) Int. Cl.
*H04L 27/06* (2006.01)
(52) U.S. Cl. ............... 375/340; 375/316; 375/295
(58) Field of Classification Search ........... 375/340, 375/316, 295
See application file for complete search history.

(56) References Cited

U.S. PATENT DOCUMENTS

| | | | |
|---|---|---|---|
| 3,740,151 A | | 6/1973 | Chaney et al. |
| 4,011,451 A | | 3/1977 | Nelson |
| 4,234,929 A | * | 11/1980 | Riley, Jr. ............... 708/101 |
| 4,276,475 A | | 6/1981 | Nelson |
| 4,457,006 A | * | 6/1984 | Maine .................. 375/333 |
| 4,498,774 A | | 2/1985 | Yeung et al. |
| 2,987,680 A | | 6/1991 | Israel |
| 5,168,326 A | | 12/1992 | Tokieda et al. |
| 5,209,231 A | | 5/1993 | Cote et al. |
| 5,276,376 A | | 1/1994 | Puskas |
| 5,286,941 A | | 2/1994 | Bel |
| 5,477,327 A | | 12/1995 | Bergman |
| 5,572,168 A | | 11/1996 | Kasturia |
| 5,621,528 A | | 4/1997 | Rokos |
| 5,625,324 A | | 4/1997 | Hsu et al. |
| 5,812,591 A | * | 9/1998 | Shumaker et al. ........ 375/147 |
| 5,822,067 A | | 10/1998 | Yanik |
| 5,896,198 A | | 4/1999 | Chou et al. |
| 5,909,642 A | * | 6/1999 | Suzuki ................. 455/114.3 |

(Continued)

FOREIGN PATENT DOCUMENTS

EP   0 438 465   7/1991

(Continued)

OTHER PUBLICATIONS

Goree, "Double lock-in detection for recovering weak coherent radio frequency signals," Rev.Sci.Instrum., vol. 56, No. 8, Aug. 1985.*

(Continued)

*Primary Examiner*—Juan A Torres
(74) *Attorney, Agent, or Firm*—David Silverstein; Andover-IP-Law

(57) ABSTRACT

The present invention provides a method, circuit and system for phase-sensitive detection and recovery of complex signals of interest using a double reference lock-in detector. A double reference lock-in detector may have two or more reference signal sources whose signals are first combined, producing a composite (e.g., inter-modulation) reference signal. This signal is then mixed with an input signal, yielding the desired selectivity at the frequency(ies) of interest. A second embodiment uses external reference signals, synchronizing internal references to these before combining the reference signals. Such detectors may used in chiral detection systems for recovering predetermined signals of interest associated with chiral properties of a sample being tested.

17 Claims, 3 Drawing Sheets

U.S. PATENT DOCUMENTS

| | | | |
|---|---|---|---|
| 6,133,804 A * | 10/2000 | Wagner et al. | 332/127 |
| 6,310,522 B1 | 10/2001 | Wang et al. | |
| 6,327,037 B1 | 12/2001 | Chou et al. | |
| 6,466,320 B1 | 10/2002 | Kawamura et al. | |
| 6,574,022 B2 | 6/2003 | Chow et al. | |
| 6,661,297 B2 | 12/2003 | Pepper | |
| 6,728,528 B1 * | 4/2004 | Loke | 455/318 |
| 6,833,764 B1 * | 12/2004 | Dean | 331/2 |
| 2003/0098746 A1 | 5/2003 | Aikawa et al. | |
| 2004/0046613 A1 | 3/2004 | Wissell | |
| 2004/0070766 A1 | 4/2004 | Szafraniec | |
| 2004/0136470 A1 * | 7/2004 | DeBruyn et al. | 375/297 |
| 2005/0062547 A1 * | 3/2005 | Reuven | 331/10 |

FOREIGN PATENT DOCUMENTS

| | | |
|---|---|---|
| EP | 0 905 506 | 3/1999 |
| EP | 1 065 497 | 1/2001 |
| EP | 1 096 248 | 5/2001 |
| EP | 1 231 455 | 8/2002 |
| EP | 1 253 715 | 10/2002 |
| EP | 0 805 352 | 3/2003 |
| JP | 2002 190780 | 7/2005 |
| WO | WO 01/06918 | 2/2001 |
| WO | WO 02/25235 | 3/2002 |
| WO | WO 03/029790 | 4/2003 |

OTHER PUBLICATIONS

Mark A. Kramer, Robert W. Boyd, Lloyd W. Hillman, and C. R. Stroud, Jr., XP-002351747 "Propagation of Modulated Optical Fields Through Saturable-absorbing Media: A General Theory of Modulation Spectroscopy," Journal of the Optical Society of America B., vol. 2, No. 9, Sep. 1, 1985, pp. 1444-1445.

Phillip Gibbs, Mark Kimmel, Andreas Bommarius and Rick Trebino, "Magneto-optical Phase Enantiomeric Detector", Conference on Lasers and Electro-Optics (CLEO) 2002, Technical Digest, Post Conference Edition, Long Beach, CA, May 19-24, 2002, pp. 408-409—vol. 73, May 19, 2002 XP010606885.

National Semiconductor Application Note 597 "Current Feedback Amplifiers", Hans Palouda, pp. 1-10, Jun. 1989.

International Search Report dated Nov. 23, 2005, for PCT/US2005/022893.

High-Performance Modular Digital Lock-In Amplifier, Rev. Sci. Instrum. vol. 66 No. (6), Jun. 1995 1995 American Institute of Physics pp. 3697-3702.

Multiple-Channel Digital Lock-In Amplifier With PPM Resolution, Rev. Sci. Instrum. vol. 65, No. 3, Mar. 1994, 1994 American Institute of Physics, pp. 747-750.

V. McOmber, "Swept Coherent-heterodyne Techniques Provide High Resolution,"—XP-001208118, Laser Focus World, vol. 38, No. 5, May 2002, pp. 173-178.

International Search Report dated Feb. 14, 2006, for PCT/US2005/022893.

Fabrizio Barone, Enrico Calloni, Luciano Difiore, Aniello Grado, Leopoldo Milano and Guido Russo, "High-Performance Modular Digital Lock-in Amplifier," Rev. Sci. Instrum., vol. 66, No. 6, Jun. 1995, pp. 3697-3702.

Pierre-Alain Probst and Alain Jaquier, "Multiple-Channel Digital Lock-in Amplifier with PPM Resolution," Rev. Sci. Instrum. vol. 65 No. 3, Mar. 1994, pp. 747-750.

E. B. Alexandrov and V. S. Zapasskii, "Millisecond Sensitivity in Polarimetric Measurements," Opt. Spectrosc, vol. 41, No. 5, Nov. 1976, pp. 502-504.

V. S. Zapasskii, "Depression of Excess Light Noise In Polarimetric Measurements," Opt. Spectrosc.(USSR) 47 (4), Oct. 1979, pp. 450-451.

V. S. Zapasskii, "High-Sensitivity Polarimeter Based on the ILA-120 Argon Laser," Opt. Spectrosc. (USSR) 52(6), Jun. 1982, pp. 667-669.

Jonathan D. Spear and Richard E. Russo, Low Noise Position Sensitive Detector for Optical Probe Beam Deflection Measurements, Rev. Sci. Instrum., vol. 67, No. 7, Jul. 1996, pp. 2481-2484.

Edward Voigtman, "Effect of Source 1/f Noise on Optical Polarimeter Performance," Anal. Chem. vol. 64, No. 21, Nov. 1, 1992, pp. 2590-2595.

Oleg Mitrofanov, "Laser Excess Noise Reduction in Optical Phase-Shift Measurements," Applied Optics, vol. 42, No. 14, May 10, 2003, pp. 2526-2531.

José A. Ferrari, César D. Perciante, Alejandro Lagos, Erna M. Frins, "Improved Method For Faraday Current Sensor Data Processing,"Optics Communications 199, Nov. 15, 2001, pp. 77-81.

D. Chauvat, J. Guéna, Ph. Jacquier, M. Lintz, M. A. Bouchiat, M.D. Plimmer and C.W. Goodwin, "Magnification of a Tiny Polarisation Rotation by a Dichroic Plate in Balanced Mode Polarimetry," Optics Communications 138, Jun. 1, 1997, pp. 249-252.

Joé A. Ferrari, Alfredo Dubra, Alfredo Arnaud, and Daniel Perciante, "Current Sensor Using Heterodyne Detection," Applied Optics, vol. 38, No. 13, May 1, 1999, pp. 2808-2811.

José A. Ferrari, César D. Perciante, Alfredo Dubra, Alfredo Arnaud, and Erna M. Frins, "Alternating Current Sensor with Second-Harmonic Detection," Applied Optics, vol. 39,No. 25, Sep. 1, 2000, pp. 4638-4640.

M. Lintz, J. Guéna, M.-A. Bouchiat, and Chauvat, "Demonstration of an Optical Polarization Magnifier with Low Birefringence," Rev. Sci. Instrum. vol. 76, 043102, (2005), pp. 043102-1-043102-4.

Alfredo Arnaud, Fernando Silveira, Erna M. Frins, Alfredo Dubra, César D. Perciante, and José A. Ferrari, "Precision Synchronous Polarimeter with Linear Response for the Measurement of Small Rotation Angles," Applied Optics, vol. 39, No. 16, Jun. 1, 2000, pp. 2601-2604.

L. A. Barragán, J. I. Artigas, R. Alonso and F. Villuendas, "A Modular, Low-cost, Digital Signal Processor-Based Lock-in Card for Measuring Optical Attenuation," Rev. Sci. Instrum., vol. 72, No. 1, Jan. 2001, pp. 247-251.

Aloke Jain, Jayant Kumar, Fumin Zhou, Lian Ll and Sukant Tripathy, "A Simple Experiment for Determining Verdet Constants Using Alternating Current Magnetic Fields," Am. J. Phys., vol. 67, No. 8, Aug. 1999, pp. 714-717.

K. Turvey, "Determination of Verdet Constant from Combined Ac and Dc Measurements," Rev. Sci. Instrum., vol. 64, No. 6, Jun. 1993, pp. 1561-1568.

Charles A. Goss, Douglas C. Wilson, and William E. Weiser, "Flow Injection Analysis with High-Sensitivity Optical Rotation Detection," Anal. Chem. vol. 66, No. 19, Oct. 1, 1994, pp. 3093-3101.

Hirofumi Kawazumi, Hideki Nishimura, Yukiaki Otsubo and Teiichiro Ogawa, "Universal On-Line Detector For High-Performance Liquid Chromatography Via Magneto Rotation," Talanta, vol. 38, No. 9, 1991, pp. 965-969.

Glenn A. Laguna, "Source Noise Reduction in Diode Laser Spectroscopy Using the Faraday Effect," Applied Optics, vol. 23, No. 13, Jul. 1, 1984, pp. 2155-2158.

J. Koch, A. Zybin, and K. Niemax, "Narrow and Broad Band Diode Laser Absorption Spectrometry—Concepts, Limitations and Applications," Spectrochimica Acta Part B 57 (2002) pp. 1547-1561.

Vladimir Liger, Alexander Zybin, Yurii Kuritsyn, and Kay Niemax, "Diode-Laser Atomic-Absorption Spectrometry by the Double-Beam-Double-Modulation Technique," Spectrochimica Acta Part B 52 (1997) pp. 1125-1138.

Rongjun Wang, Yangqin Chen, Peipei Cai Jingjing Lu, Zhiyi Bi, Xiaohua Yang and Longsheng Ma, "Optical Heterodyne Velocity Modulation Spectroscopy Enhanced by a Magnetic Rotation Effect," Chemical Physics Letters 307 (1999) pp. 339-342.

Norman P. Barnes and Larry B. Petway, "Variation of the Verdet Constant With Temperature of Terbium Gallium Garnet," J. Opt. Soc. Am. B, vol. 9, No. 10, Oct. 1992, pp. 1912-1915.

E. J. Gillham, "A High-Precision Photoelectric Polarimeter," Journal of Scientific Instruments, vol. 34, Nov. 1957, pp. 435-439.

Z. P. Wang, Q. B. Li, R.Y. Feng, H. L. Wang, Z. J. Huang, and J. H. Shi, "Effects of the Polarizer Parameters upon the Performance of an Optical Current Sensor," Optics & Laser Technology 36, 2004, pp. 145-149.

P. G. L. Mills and M. O. J. Hawksford, "Transconductance Power Amplifier Systems for Current-Driven Loudspeakers," J. Audio Eng. Soc., vol. 37, No. 10, Oct. 1989, pp. 809-822.

P. G. L. Mills and M. O. J. Hawksford, "Distortion Reduction in Moving-Coil Loudspeaker Systems Using Current-Drive Technology," J. Audio Eng. Soc., vol. 37, No. 3, Mar. 1989, pp. 129-148.

James Karki, "Voltage Feedback Vs. Current Feedback Op Amps," Literature No. SLVA051, Nov. 1998, pp. 1-10, A-1-6.

Debbie Brandenburg, "Current vs. Voltage Feedback Amplifiers," National Semiconductor Corporation, Jan. 1998, pp. 1-6.

Debbie Brandenburg, "Current vs. Voltage Feedback Amplifiers, "2002 National Semiconductor Corporation, OA-30, Jan. 1998, pp. 1-5.

Arne Buck, "Current-Feedback Myths Debunked," 2002 National Semiconductor Corporation OA-20, Jul. 1992, pp. 1-4.

W. L. L. Lenders, "The Orthocyclic Method of Coil Winding," Philip Technical Review, vol. 23, No. 12, Oct. 16, 1962, pp. 365-404.

Daniel A. DeAntonio, "Soft Magnetic Ferritic Stainless Steels," Advanced Materials & Processes, Oct. 2003, pp. 29-32.

Carlo Bertucci, Vincenza Andrisano, Vanni Cavrini and Ettore Castiglioni, "Reliable Assay of Extreme Enantiomeric Purity Values by a New Circular Dichroism Based HPLC Detection System," Chirality 12:84-92 (2000).

Prasad L. Polavarapu, "Optical Rotation: Recent Advances in Determining the Absolute Configuration," Chirality 14:768-781, 2002.

M. Bouchiat, D. Chauvat, J. Guéna, Ph. Jacquier, M. Lintz, and M. D. Plimmer, "High Precision Balanced Mode Polarimetry With a Pulsed Laser Beam," Optics Communications 119, Sep. 1, 1995 pp. 403-414.

Timothy W. King, Gerard L. Coté, Roger McNichols, Marcel J. Goetz, Jr., "Multispectral Polarimetric Glucose Detection Using a Single Pockels Cell," Optical Engineering, vol. 33, No. 8 Aug. 1994, pp. 2746-2753.

"The Benefits of DSP Lock-In Amplifiers," Optronic Laboratories, Inc., Application Note (A12), Revision A, Sep. 1996, pp. 1-8.

Donald R. Bobbit, and Sean W. Linder, "Recent Advances in Chiral Detection For High Performance Liquid Chromatography," Trends In Analytical Chemistry, vol. 20, No. 3, 2001, pp. 111-123.

Peter Rozea, "Chiral Compound Analyses and Faraday Polarimetry" Application Note, Nov. 2001, pp. 20-23.

M. G. Finn, "Emerging Methods for the Rapid Determination of Enantiomeric Excess," Chirality 14:534-540, 2002.

H. J. Lozykowski, T. Li and Z. I. Akir, "Digital Spectropolarimeter For The Measurement of Optical Polarization," Rev. Sci. Instrum., vol. 63, No. 9, Sep. 1992, pp. 4096-4101.

Andreas Mandelis, Stefano Paoloni and Lena Nicolaides, "Novel Lock-In Waveform Technique for Signal-to-Noise Ratio and Dynamic-Range Enhancement in High Noised Photothermal Experiments," Analytical Sciences, vol. 17, Apr. 2001, pp. s5-s8.

Roger J. McNichols, Gerard L. Coté, Marcel J. Goetz, Jr., and Timothy W. King, "Linear Superposition of Specific Rotation for the Detection of Glucose" IEEE, 1993, pp. 1549-1550.

Brent D. Cameron and Gerard L. Coté, "Polarimetric Glucose Sensing in Aqueous Humor Utilizing Digital Closed-Loop Control," 18$^{tth}$ Annual International Conference of the IEEE Engineering in Medicine and Biology Society, Amsterdam 1996, pp. 204-205.

Aidan F. Browne, Todd R. Nelson and Robert B. Northrop, "Microdegree Polarimetric Measurement of Glucose Concentrations for Biotechnology Applications," IEEE, 1997, pp. 9-10.

Sunghoon Jang, Zhi Yang, Martin D. Fox and Dan Censor, "Double Lock-In Amplifier Faraday Rotation Glucometer," IEEE 2000, pp. 107-108.

Marcel J. Goetz, Jr., Martin D. Fox, MD. PH.D, and Robert B. Northrop, PH.D, "Microdegree Polarimetry Using A Diode Laser For Glucose Detection," IEEE, 1992, pp. 97-98.

Sunghoon Jang, and Martin D. Fox, "Double Lock-In Concept For More Glucose Detection," IEEE, 1999, pp. 122-124.

Michael La Marca, "Laser Interferometer Gravitational Wave Observatory," California Institute of Technology, Massachusetts Institute of Technology, Surf Final Report, Sep. 7, 2001, pp. 1-17.

C. Denise Caldwell, "Digital Lock-in Technique For Measurement of Polarization of Radiation," Optics Letters, vol. 1, No. 3, Sep. 1977, pp. 101-103.

Harry G. Brittain, "Applications of Chiroptical Spectroscopy for the Characterization of Pharmaceutical Compounds," Journal of Pharmaceutical and Biomedical Analysis 17, 1998, pp. 933-940.

"FM Spectroscopy with Tunable Diode Lasers" Application Note 7, New Focus, 2001, pp. 1-11.

Dr. Theodore Oakberg, "Linear Birefringence and Optical Rotation," PEM- 90 Application Note, Hinds Instruments, Inc., 1993, pp. 1-6.

Roger J. McNichols, Brent D. Cameron and Gerard L. Coté, "Development of a Non-Invasive Polarimetric Glucose Sensor," IEEE, Apr. 1998, pp. 1-3.

International Search Report dated Aug. 29, 2005, for PCT/US2005/015312 (corresponding to the present application).

International Search Report dated Sep. 27, 2005 for 9524.008-304 (corresponding to U.S. Patent Application No. 11/168,296).

XP-001121554, Chien Chou, Yen-Chuen Haung, Ching-Mei-Feng and Ming Chang, "Amplitude Sensitive optical Heterodyne and Phase Lock-in Technique on Small Optical Rotation Angle Detection of Chiral Liquid", Jpn. J. Appl. Phys., vol. 36, Jan. 1997, pp. 356-359.

E. A. Avrutin, J. H. Marsh and E. L. Portnoi, "Monolithic and Multi-GigaHertz Mode-Locked Semiconductor Lasers: Constructions, Experiments, Models and Applications", IEE-Proc.-Optoelectron., vol. 147, No. 4, Aug. 2000, pp. 251-278.

Co-pending U.S. Appl. No. 11/168,295, Title: Systems and Methods for Chiroptical Heterodyning, Inventors: Phillip R. Gibbs et al. U.S. Filing Date: Jun. 28, 2005.

Co-pending U.S. Appl. No. 11/168,296, Title: Systems and Methods for Automated Resonant Circuit Tuning, Inventor: Phillip R. Gibbs, U.S. Filing Jun. 29, 2005.

* cited by examiner

CHIRAL MIXTURE DETECTION SYSTEM USING DOUBLE REFERENCE LOCK-IN DETECTOR

RELATED APPLICATIONS

This patent application claims priority to an earlier provisional patent application filed on May 4, 2004 and entitled "A Double Reference Lock-In Detector" by Dr. Phillip R. Gibbs. The content of this provisional patent application is hereby incorporated by reference in its entirety.

FIELD OF THE INVENTION

This invention generally relates to reference lock-in devices in receiving systems and methods and, more specifically, the invention is related to systems and methods for signal recovery using a double reference configuration for a lock-in amplifier/detector.

BACKGROUND OF THE INVENTION

Lock-in amplifiers are a form of detector particularly well suited to extract low strength narrowband signals from broadband noise. Because the lock-in amplifiers are phase sensitive, they are able to extract an input signal component at a specific frequency and phase by multiplying a reference signal against the broadband input signal. The reference signal may be from an oscillator or function generator, at any appropriate waveform (e.g., a sine wave, a square wave etc.). FIG. 1 illustrates a typical single reference lock-in amplifier 110 that is known in the prior art, where the reference from VCO (variable crystal oscillator) 115 is mixed with the input signal in mixer 120. The resulting signal may also be narrowband filtered, in the illustrated case by use of a low pass filter (LPF) 125 following mixer 120.

It is sometimes desirable to use an external reference in a lock-in amplifier. In the typical case, the VCO of the lock-in amplifier is phase-locked to the external reference, and FIG. 2 illustrates one approach to locking the internal reference signal to an external reference. As shown in FIG. 2, system 205 includes a reference 206, which provides an external reference signal to lock-in amplifier 210. System 205 also provides an input signal to lock-in amplifier 210, which includes mixer 220, LPF 225 and PLL 215 (which is further depicted in FIG. 2 to include mixer 212, integrator 213, and VCO 211). While two references are used, one external (e.g., reference 206) and one internal (e.g., PLL 215), there is still only one lock-in signal applied to the mixer 220 to extract the signal of interest from the input signal.

In addition to single lock-in amplifiers, some have suggested the use of a double lock-in to minimize noise issues at the frequency of interest. One such approach is illustrated in the article by J. Goree, "Double lock-in detection for recovering weak coherent radio frequency signals," Rev.Sci.Instrum., Vol. 56, No. 8 (August 1985). In that case, it was found that significant and problematic RF pick-up was passing unattenuated through the lock-in, rendering lock-in detection useless. By introducing a second lock-in device before the first one, it was disclosed that the second one be synchronized to a system modulation (e.g., a mechanical chopper wheel), thereby minimizing the unmodulated RF pick-up contribution at the frequency of interest.

However, the above approaches still have a common limitation in their use of a single reference signal for the lock-in with the signal of interest. In some instances a more complex, i.e., a composite, reference signal is desired to extract a signal or signals of interest. This would allow one to extract multiple signals of interest, or avoid the particular single frequencies and harmonics of each individual reference (e.g., by composite we mean a combination of two reference signals thereby yielding inter-modulation and/or its sideband/harmonic components). The single reference lock-in approach of the prior art is unable to provide an appropriate signal for lock-in in these cases.

Thus, there is a need for an improved lock-in detector or amplifier, one which allows for flexibility and ease in achieving a lock-in via a composite reference.

SUMMARY OF THE INVENTION

In accordance with the invention, various aspects of the present invention are described herein. In general, present invention provides a method, circuit and system for phase-sensitive detection and recovery of complex signals of interest. In an exemplary embodiment, a double reference lock-in detector may have two or more reference signal sources whose signals are first combined, producing a composite (e.g., inter-modulated) reference signal. This signal is then mixed with the signal of interest, yielding the desired amplification at the frequency(ies) of interest. A second embodiment uses external reference signals, synchronizing internal references to these before combining the reference signals.

In one aspect of the invention, a method is provided for recovering a signal of interest from an input signal. The method begins by receiving a first reference signal and receiving a second reference signal. The first and second reference signals may be modulation signals associated with the input signal. The method continues by generating a composite reference signal having inter-modulation products of the first reference signal and the second reference signal. The composite reference signal, which may be filtered to obtain a single sideband or inter-modulation component, is multiplied by the input signal to provide a product signal. The signal of interest is recovered from the product of the input signal and the composite reference signal. The step of recovering may further include mixing the input signal and the composite reference signal to form a mixed signal as the product. Recovering may also include filtering the mixed signal to detect and recover the signal of interest.

The method may implement the step of receiving the first reference signal by obtaining the first reference signal at a first modulation frequency from an internal signal source. Likewise, the method may implement the step of receiving the second reference signal by obtaining the second reference signal at a second modulation frequency from another internal signal source.

Alternatively, the method may implement the step of receiving the first reference signal by obtaining the first reference signal at a first modulation frequency from an external signal source and implement the step of receiving the second reference signal by obtaining the second reference signal at a second modulation frequency from another external signal source.

Further, the method may include the step of providing a first phase-locked loop signal based on the first reference signal and providing a second phase-locked loop signal based on the second reference signal. The generating step may also comprise combining the first and second phase-locked loop signals together as the composite reference signal.

In another aspect of the invention, a detection circuit is provided for recovering a signal of interest. The circuit includes a reference source, which has multiple reference generators and a combiner, and a mixer. The reference generators may be internal signal sources, such as VCO's or other types of synthesizers or oscillators. The combiner is coupled to each of the reference generators and can provide a composite reference signal responsive to signals from the reference generators. The composite reference signal is an output of the reference source at a first phase condition. The mixer is coupled to the output of the reference source and can operate to extract the signal of interest having substantially the same phase condition as the first phase condition in response to receiving an input signal. The detection circuit may also include a narrowband filter coupled to an output of the mixer for selectively providing the signal of interest.

The reference generators may be responsive to a plurality of external signal sources, respectively. Further, each of the external signal sources may be operatively coupled to a respective one of the reference generators in a phase-locked relationship. The reference generators may also be respectively associated with a plurality of modulation signals for the input signal.

In yet another aspect of the invention, a detection system for recovering a signal of interest associated with a property of a chiral mixture is provided. The system includes a first signal source modulated by a first reference signal and a magnetic field source modulated by a second reference signal. The system also has a sample cell that is responsive to the first signal source and the magnetic field source and that maintains the chiral mixture. Finally, the system includes at least one multiple-reference lock-in amplifier or detector coupled to an input signal associated with the resultant output of the sample cell. The multiple-reference lock-in detector uses the first reference signal and the second reference signals to generate an inter-modulation composite reference signal with which to extract the signal of interest.

The lock-in detector may further comprise a reference source responsive to the first reference signal and the second reference signal. The reference source may include a combiner coupled to each of the first reference signal and the second reference signal in order to provide a composite reference signal. The composite reference signal is an output of the reference source. Further, the lock-in detector may include a mixer coupled to the output of the reference source. The mixer may be operative to extract the signal of interest in response to receiving an input signal.

The detection system may also include a narrowband filter coupled to an output of the mixer for selectively providing the signal of interest. As such, the first reference signal may be coupled to a first reference generator in a phase-locked relationship and the second reference signal may be coupled to a second reference generator in a phase-locked relationship.

It is to be understood that both the foregoing general description and the following detailed description are exemplary and explanatory only and are not restrictive of the invention, as claimed. Additional advantages of the invention will be set forth in part in the description which follows, and in part will be obvious from the description, or may be learned by practice of the invention.

The accompanying drawings, which are incorporated in and constitute a part of this specification, illustrate several embodiments of the invention and together with the description, serve to explain the principles of the invention.

DESCRIPTION OF THE PREFERRED EMBODIMENT

Reference will now be made in detail to the present exemplary embodiments of the invention, examples of which are illustrated in the accompanying drawings and description that follows. Wherever possible, the same reference numbers will be used throughout the drawings to refer to the same or like parts.

Figure 1:
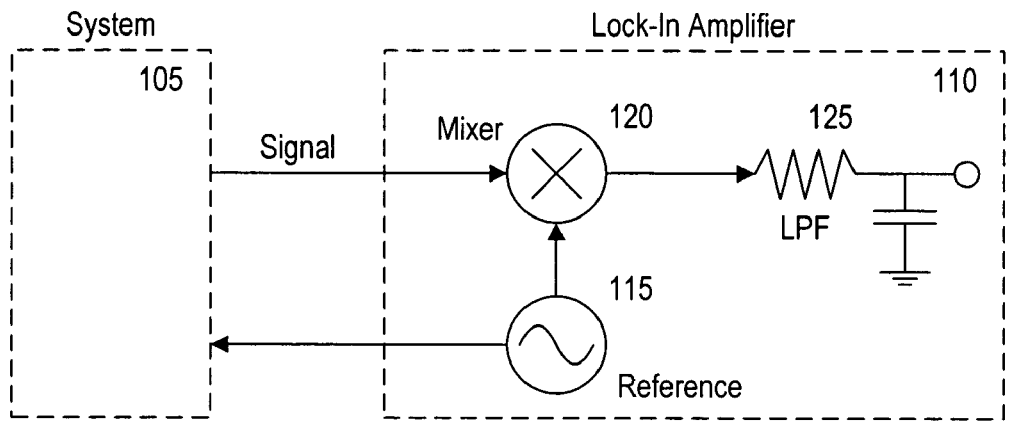
FIG. 1 is a block diagram of an illustrative prior art approach for a single reference lock-in amplifier.
Figure 2:
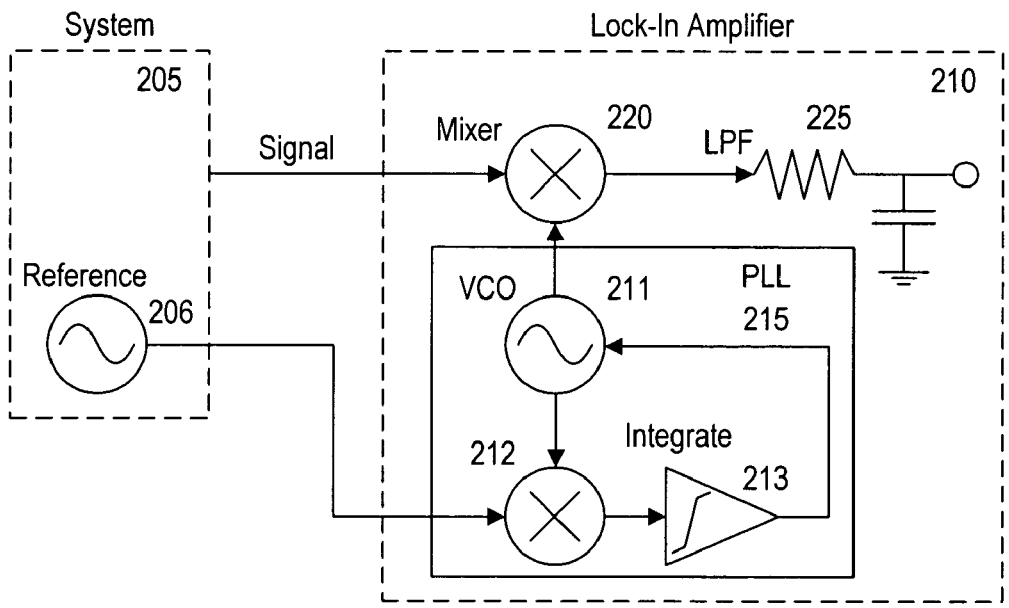
FIG. 2 is a block diagram of another illustrative prior art approach that uses an external reference to synchronize a single reference lock-in amplifier.
Figure 3:
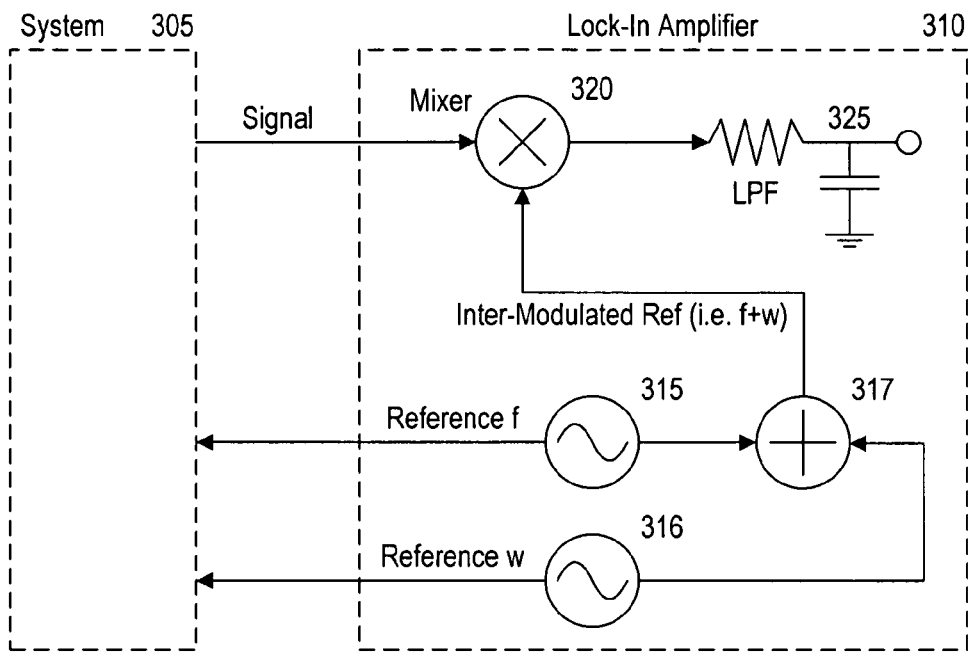
FIG. 3 is a block diagram illustrating an exemplary multi-reference lock-in amplifier according to an embodiment of the invention.
Figure 4:
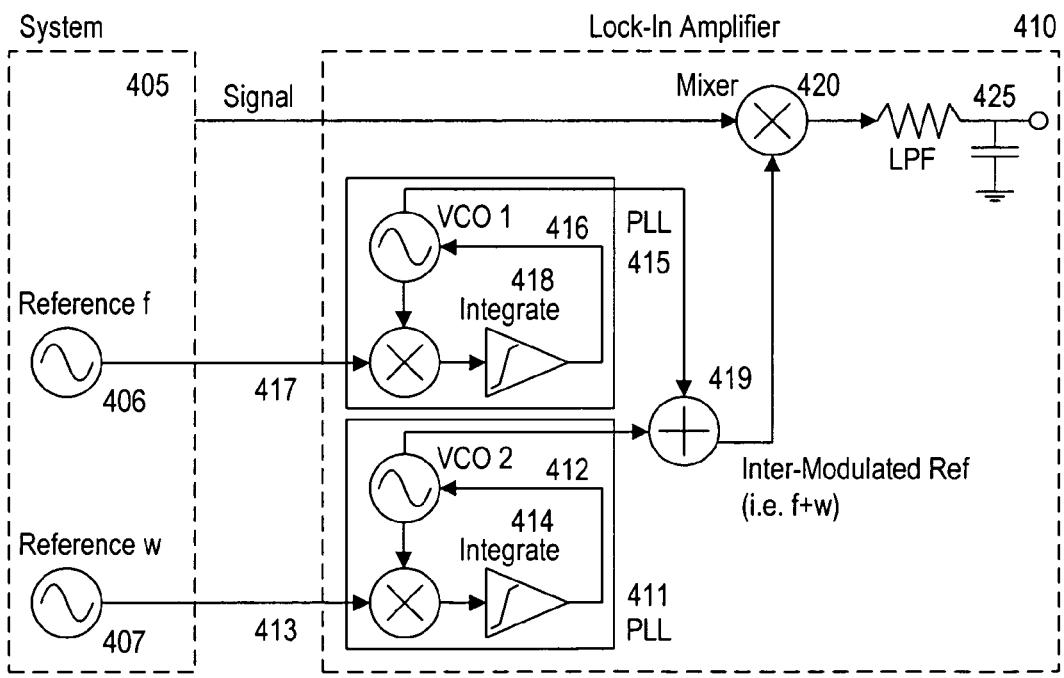
FIG. 4 is a block diagram illustrating an exemplary multi-reference lock-in amplifier using external references according to a further embodiment of the invention.

In general, the limitations of prior systems described above may be overcome by novel aspects illustrated by various embodiments of the present invention, which are illustrated by the following detailed description and in FIGS. 3 and 4. These embodiments are particularly well-suited for use in testing applications, such as the chiral analysis environment of FIG. 5. Another example chiral analysis environment useful for an implementation of the present invention is further disclosed in a prior provisional application filed on Oct. 10, 2003, entitled "Differential Optical Technique for Chiral Analysis", Ser. No. 60/510,209, and PCT WO 03/029790 A1 entitled "High-Throughput Chiral Detector and Methods for Using Same" by Dr. Phillip R. Gibbs, both of which are hereby incorporated by reference. In lieu of the single reference lock-in described in these filings, a superior result can be achieved by use of embodiments and aspects of the present invention in the analytical processes and systems previously disclosed.

With reference now to the figures and in particular with reference to FIG. 3, an exemplary representation of a multi-reference lock-in amplifier 310 is depicted in accordance with an embodiment of the invention. The system 305 and detector 310 receive reference signals f and w from two reference sources 315, 316, respectively. Both reference signals are provided to combiner 317, to generate and yield a composite reference signal (e.g., inter-modulated signal f+w, along with its sidebands). This inter-modulated composite reference signal, or at least one of its components, is then applied to mixer 320 to recover and extract the signal of interest from the input signal. In one embodiment, a filter (not shown) may be used to select a specific inter-modulation component of the composite reference signal to be applied to mixer 320. Further, a narrowband filter 325 coupled to the output of the mixer 320 may be used to help reduce noise components outside of the frequency of interest and enhance extraction of the signal of interest. This may be especially advantageous in a system where the input signal is dependent on modulation by more than one frequency, thus making it difficult to utilize a conventional lock-in detector.

While FIGS. 3 and 4 have been depicted in block diagram form, those skilled in the art will appreciate that these are functional depictions that can be readily implemented in a variety of circuits. For example, a detection circuit may be implemented with discrete components, integrated circuits, or software running on special or general purpose processors such as a computer. For example, those skilled in the art will appreciate that such a computer or processor includes a microprocessor, digital signal processor, or application specific integrated circuit having DSP functionality. The particular implementation is a matter of design choice.

In the embodiment illustrated in FIG. 5 and described further below, the implementation is digital using digital signal processors. Thus, for a fixed experiment, one can typically generate predetermined sine tables (also known as wavetables) for all references (driving and inter-modulated), so that no additional computation is required once the initial tables are generated. Those skilled in the art will appreciate that such wavetables are commonly used with digital signal processors. Similarly, any inter-modulation frequency combination of the two fundamental frequencies (f and w) can be generated and tracked by changing the mathematical mixing of the two references and storing these. The desired reference values can then be applied by mathematical mixing with the input signal, taken in discrete portions, in order to detect frequencies of interest in selected sidebands and inter-modulation frequencies (e.g., f+w, f−w, 2f+w, 2f−w, 3f+w, f+2w, etc . . . ).

The phase dependence of the lock-in analysis may be avoided by performing a second lock-in analysis utilizing a phase-shifted form of the applied reference (e.g., the composite reference signal having inter-modulated signal f+w). In other words, the digitally implemented lock-in detector may use an in-phase version of the composite reference signal and further use a phase-shifted version of the composite reference signal during its analysis. The phase shift is preferred to be at or substantially near ninety degrees in order to provide a substantially quadrature relationship between signals. By trigonometric relation, an absolute signal magnitude is computed that is dependent only on the magnitude of the desired frequency component. Phase information may be extracted using the inverse tangent of the reference and the quadrature analytical signals. By use of a single reference clock for both the driving and the analysis waveforms (i.e., those signals generated by wavetables), the relative phase of the analytical components can also be considered absolute, changing only due to induced phase-shifts in the observed signal. If one does not couple the two reference waveforms and the analysis waveform in such a manner, the resulting phase information will be arbitrary and dependent on the initial start up conditions of the analysis.

FIG. 4 illustrates another embodiment according to the invention. Referring now to FIG. 4, a double reference lock-in amplifier 410 receives reference signals f and w from external reference signal sources 406, 407 of system 405. These external reference signals from system 405 are phase-locked with internal sources (e.g., VCOs, crystal oscillators, frequency synthesizer, etc.) 412, 416 in phase-locked loops (PLL) 411, 415. As shown in FIG. 4, PLL 415 includes VCO 416, mixer 417 and integrator 418. Likewise, PLL 411 is shown to include VCO 412, mixer 413 and integrator 414. In this manner, the PLLs operate as types of reference generators within a reference source (despite being driven by external reference signal sources). As such, the PLLs may be considered to generate what is generally referred to as different phase-locked loop signals provided to a combiner when producing the composite reference signal.

Combiner 419 receives the output of each PLL 415, 411 and produces the desired composite reference signal (e.g., inter-modulated reference (f+w) and/or sidebands/harmonics as desired). This composite reference signal is then applied to mixer 420 to extract and recover the signal of interest from the input signal. A low pass filter (LPF) 425 may be used to help remove noise components outside of the selected frequency band and enhance extraction and recovery of the desired signals of interest.

Thus, the embodiments illustrated in FIGS. 3 and 4 provide signals dependent on two modulation frequencies. This allows one to better extract inter-modulation signals of interest and yields a better signal to noise ratio (SNR) than conventional single reference signal lock-in approaches. This improved performance occurs because an inter-modulated signal can be obtained at a much higher chopping rate (e.g., f+w, yielding 1/f performance improvement) and down modulation is possible to facilitate analysis of higher frequency responses (e.g., f−w may be computationally tractable as opposed to f+w for some frequencies). Those skilled in the art will appreciate that as such, it will help with high frequency situations when gathering more data becomes easier using f−w as opposed to f+w. Furthermore, performance may be improved using an embodiment of the present invention as additional analytical information can be obtained from the modulated systems response at multiple sidebands (e.g., f+w correlates to Verdet and 2f+w correlates to optical rotation in FIG. 5), and noise introduced with the chopping of the system at each of the fundamentals (e.g., f and w) will not occur at the inter-modulated frequencies.

The embodiments described in FIGS. 3 and 4 may be implemented in a variety of testing environments or other applications requiring signal recovery. In one example, the testing environment may be a chiral testing environment as illustrated in FIG. 5. In that example, a double reference lock-in detector is utilized in a chiral heterodyne application for the recovery of desired analytical signals of interest, as disclosed in U.S. Provisional patent application Ser. No. 60/584,105 entitled "Systems and Methods for Chiroptical Heterodyning" by Dr. Phillip R. Gibbs, which is hereby incorporated by reference.

Figure 5:
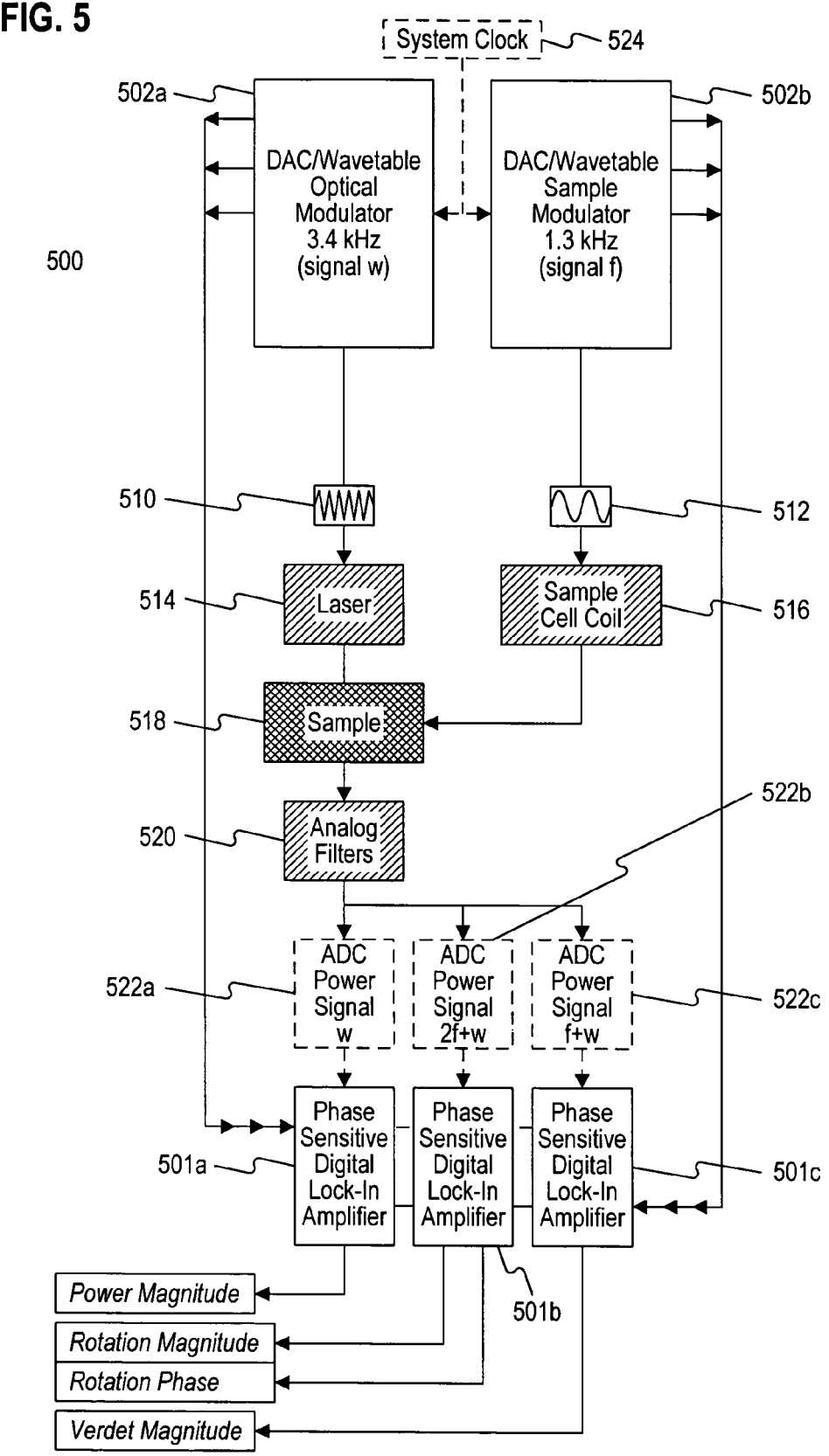
FIG. 5 is a block diagram of an exemplary application environment and representative signal flow diagram that uses a double reference lock-in detector system according to an embodiment of the invention.

Referring now to FIG. 5, an exemplary chiral detection system 500 is conceptually illustrated that uses a digitally implemented double-reference lock-in amplifier in the receiver side of the system consistent with the principles of the present invention. The system 500 uses a common system clock 524 to drive the system's components, which include digital-to-analog (DAC)/wavetables 502a-b as modulation signal sources, laser 514, sample cell coil 516, sample 518, filters 520, and one or more analog-to-digital (ADC) units 522a-c coupled to one or more digital lock-in amplifiers 501a-c. DAC/wavetable 502a provides a signal w 510 that modulates an optical beam being applied to sample 518 from laser 514. DAC/wavetable 502b provides a signal f 512 that modulates a magnetic field 512 exposed to the sample 518 via the sample cell coil 516. Thus, the DAC/wavetables 502a-b generate modulation signals used to stimulate sample 518 based upon a common clock 524.

The light transmitted through sample 518 carries information about the sample in its intensity and polarization state. One or more photodiodes (not shown) may be used to detect the amplitude of the transmitted light and produce electrical signals representative of the transmitted light. The electrical signal may be filtered by filters 520 to produce signals and converted back to digital form by ADC units 522a-c using the same system clock 524. In one embodiment, the electrical signal is filtered along four filter paths to produce signals that are acquired by the ADC units. In this manner, the ADC units provide a data stream (a digital representative of an input signal) to the lock-in amplifiers.

In this example, the digital lock-in amplifiers 501a-c are implemented in a digital signal processor that recovers each of the filtered signals at w, 2f+w, and f+w, respectively. While lock-in amplifier 501*a* need only rely upon a single reference signal (signal w), lock-in amplifiers 501*b-c* are implemented to rely upon two reference signals (e.g., modulation signal w from DAC/wavetable 502*a* and modulation signal f from DAC/wavetable 502*b*) to create the composite reference signal having the appropriate inter-modulation products for use in their respective phase-sensitive lock-in analysis for signals of interest at 2f+w and f+w. In this case the composite reference is precomputed and stored as separate wavetables for 2f+w and f+w. These composite wavetables are linked to the same system clock as the driving frequency references to maintain a non-arbitrary phase relationship in the recovered system response at 2f+w and f+w.

In summary, embodiments of the present invention provide an improved lock-in unit, device, or system. Those skilled in the art will appreciate how a variety of alternatives are possible for the individual elements, and their arrangement, described above, while still falling within the scope of the invention. Thus, while it is important to note that the present invention has been described in the context of a particular double lock-in approach, those of ordinary skill in the art will appreciate that the components and processes of the present invention are capable of being implemented by any convenient hardware and/or software configuration, and extends to any lock-in detector with two or more reference sources.

In conclusion, the above description has been presented for purposes of illustration and description of various embodiments of the invention, but is not intended to be exhaustive or limited to the form disclosed. This embodiment was chosen and described in order to explain the principles of the invention, show its practical application, and to enable those of ordinary skill in the art to understand how to make and use the invention. Many modifications and variations will be apparent to those of ordinary skill in the art. Thus, it is intended that the specification and examples be considered as exemplary only, with a true scope and spirit of the invention being indicated by the following claims.

What is claimed is:

1. A method for recovering a signal of interest associated with a property of a chiral mixture being tested within a detection system having a combiner, comprising:
   receiving a first reference signal at an input to the combiner;
   receiving a second reference signal at a second input to the combiner, the first reference signal and the second reference signal being generated with a common clock and used to modulate a driving signal applied to the chiral mixture;
   generating a composite reference signal on an output of the combiner, wherein the composite reference signal has inter-modulation products of the first reference signal and the second reference signal; and
   multiplying the composite reference signal by an input signal exposed to the chiral mixture to provide a product signal; and
   recovering phase information on the signal of interest from the product of the input signal and the composite reference signal.

2. The method of claim 1, wherein the recovering step further comprises filtering the composite reference signal to select an inter-modulation component of the composite reference signal before mixing with the input signal to form a mixed signal as the product.

3. The method of claim 1, wherein the recovering step further comprises filtering the mixed signal to detect the signal of interest.

4. The method of claim 1, wherein the step of receiving the first reference signal further comprises obtaining the first reference signal at a first modulation frequency from an internal signal source; and
   wherein the step of receiving the second reference signal further comprises obtaining the second reference signal at a second modulation frequency from another internal signal source.

5. The method of claim 1, wherein the step of receiving the first reference signal further comprises obtaining the first reference signal at a first modulation frequency from an external signal source; and
   wherein the step of receiving the second reference signal further comprises obtaining the second reference signal at a second modulation frequency from another external signal source.

6. The method of claim 5 further comprising the step of providing a first phase-locked loop signal based on the first reference signal and providing a second phase-locked loop signal based on the second reference signal; and
   wherein the generating step further comprises combining the first and second phase-locked loop signals together as the composite reference signal having inter-modulation components related to the first reference signal and the second reference signal.

7. A detection circuit for recovering a signal of interest associated with a property of a chiral mixture, comprising:
   a reference source further comprising,
      plurality of reference generators each of which provides a signal that modulates a driving signal applied to the chiral mixture;
      a combiner coupled to each of the reference generators, the combiner being operative to provide an inter-modulation composite reference signal responsive to signals from the reference generators, the composite reference signal being an output of the reference source at a first phase condition; and
   a mixer coupled to the output of the reference source, the mixer being operative to extract the signal of interest having substantially the same phase condition as the first phase condition in response to receiving an input signal exposed to the chiral mixture, the input signal being related to the driving signal applied to the chiral mixture.

8. The detection circuit of claim 7, further comprising a narrowband filter coupled to an output of the mixer for selectively providing the signal of interest.

9. The detection circuit of claim 7, wherein the plurality of reference generators are internal signal sources.

10. The detection circuit of claim 7, wherein the plurality of reference generators are respectively responsive to a plurality of external signal sources.

11. A detection system for recovering a signal of interest associated with a property of a chiral mixture, comprising:
   a first source modulated by a first reference signal;
   a second source modulated by a second reference signal, the first and second source being generated with a common clock;
   a sample cell responsive to the modulation provided by the first signal source and the second signal source, the sample cell maintaining the chiral mixture, the sample cell providing a resultant output; and
   a multiple-reference lock-in detector coupled to an input signal associated with the resultant output of the sample cell, the multiple-reference lock-in detector further comprising a combiner that uses the first reference signal and the second reference signals to generate an inter-modulation composite reference signal and a multiplier with which to extract the signal of interest based upon the inter-modulation composite reference signal as a first input to the multiplier and the input signal as a second input to the multiplier, wherein a phase condition of the inter-modulation composite reference signal is related to the first and second reference signals imparting modulation applied to the sample cell.

12. The detection system of claim 11, wherein the second source is a magnetic field source.

13. The detection system of claim 11, wherein the second source is an electric field source.

14. The detection system of claim 11, wherein the lock-in detector further comprises:
a reference source responsive to the first reference signal and the second reference signal, the reference source including combiner coupled to each of the first reference signal and the second reference signal in order to provide the inter-modulation composite reference signal as an output of the reference source; and wherein the mixer is coupled to the output of the reference source, the mixer being operative to extract the signal of interest in response to receiving the input signal by multiplying the input signal by the inter-modulation composite reference signal.

15. The detection system of claim 14, further comprising a narrowband filter coupled to an output of the mixer for selectively providing the signal of interest.

16. The detection system of claim 15, wherein the first reference signal is coupled to a first reference generator in a phase-locked relationship and the second reference signal is coupled to a second reference generator in a phase-locked relationship.

17. The detection system of claim 11, further including a filter operatively coupled between the reference source and the mixer, the filter being operative to select an inter-modulation component from the inter-modulation composite reference signal.

* * * * *